US010869667B2

(12) United States Patent
Kapadia

(10) Patent No.: US 10,869,667 B2
(45) Date of Patent: Dec. 22, 2020

(54) SURGICAL FASTENER APPLYING APPARATUS

(71) Applicant: Covidien LP, Mansfield, MA (US)

(72) Inventor: Salman Kapadia, Madhya Pradesh (IN)

(73) Assignee: Covidien LP, Mansfield, MA (US)

(*) Notice: Subject to any disclaimer, the term of this patent is extended or adjusted under 35 U.S.C. 154(b) by 315 days.

(21) Appl. No.: 15/995,489

(22) Filed: Jun. 1, 2018

(65) Prior Publication Data
US 2018/0271525 A1 Sep. 27, 2018

Related U.S. Application Data

(63) Continuation of application No. 14/372,469, filed as application No. PCT/US2013/020838 on Jan. 9, 2013, now Pat. No. 9,987,007.
(Continued)

(51) Int. Cl.
A61B 17/072 (2006.01)
A61B 17/28 (2006.01)
(Continued)

(52) U.S. Cl.
CPC .... A61B 17/07207 (2013.01); A61B 17/2812 (2013.01); A61B 17/2833 (2013.01);
(Continued)

(58) Field of Classification Search
CPC ............ A61B 17/2812; A61B 17/2816; A61B 17/282; A61B 17/2833; A61B 17/2841;
(Continued)

(56) References Cited

U.S. PATENT DOCUMENTS 2,853,074 A * 9/1958 Olson ................ A61B 17/1152
227/177.1
3,604,561 A 9/1971 Mallina et al.
(Continued)

FOREIGN PATENT DOCUMENTS

CN 101543417 A 9/2009
CN 102056553 A 5/2011
(Continued)

OTHER PUBLICATIONS

Chinese Office Action dated Jan. 27, 2016, issued in Chinese Application No. 201380006085.
(Continued)

Primary Examiner — Andrew M Tecco
(74) Attorney, Agent, or Firm — Carter, DeLuca & Farrell LLP

(57) ABSTRACT

A surgical fastener applying apparatus including a cartridge supporting section and an anvil supporting section. The cartridge supporting section includes a distal section and a proximal section and the anvil supporting section and cartridge supporting section are configured to clamp tissue therebetween. The anvil supporting section has a distal fastener receiving region, a proximal clamping region and an intermediate region between the fastener receiving region and the clamping region. The proximal clamping region is positioned on a first side of the cartridge supporting section and the fastener receiving region is positioned on a second opposing side of the cartridge supporting section.

18 Claims, 5 Drawing Sheets

Related U.S. Application Data

(60) Provisional application No. 61/587,879, filed on Jan. 18, 2012.

(51) Int. Cl.
  *A61B 90/00* (2016.01)
  *A61B 17/32* (2006.01)
  *A61B 17/00* (2006.01)

(52) U.S. Cl.
  CPC .............. *A61B 2017/0023* (2013.01); *A61B 2017/00477* (2013.01); *A61B 2017/0725* (2013.01); *A61B 2017/07214* (2013.01); *A61B 2017/07271* (2013.01); *A61B 2017/320052* (2013.01); *A61B 2090/033* (2016.02); *A61B 2090/0813* (2016.02)

(58) Field of Classification Search
  CPC .... A61B 17/07207; A61B 2017/00477; A61B 2017/2825; A61B 2017/2829
  See application file for complete search history.

(56) References Cited

U.S. PATENT DOCUMENTS

| | | | |
|---|---|---|---|
| 3,873,016 A | | 3/1975 | Fishbein |
| 4,429,695 A | * | 2/1984 | Green .............. A61B 17/07207 227/176.1 |
| 5,445,304 A | * | 8/1995 | Plyley .............. A61B 17/07207 227/176.1 |
| 5,501,689 A | | 3/1996 | Green et al. |
| 6,131,789 A | * | 10/2000 | Schulze ........... A61B 17/07207 227/175.2 |
| 9,987,007 B2 | | 6/2018 | Kapadia |
| 2004/0007608 A1 | * | 1/2004 | Ehrenfels ......... A61B 17/07207 227/176.1 |
| 2005/0222616 A1 | * | 10/2005 | Rethy .................. A61B 17/105 606/215 |
| 2009/0308907 A1 | * | 12/2009 | Nalagatla ......... A61B 17/07207 227/175.2 |
| 2010/0072251 A1 | * | 3/2010 | Baxter, III .......... A61B 17/105 227/175.2 |
| 2010/0230468 A1 | | 9/2010 | Viola |
| 2013/0261661 A1 | * | 10/2013 | Piraka ................ A61B 17/105 606/219 |

FOREIGN PATENT DOCUMENTS

| | | |
|---|---|---|
| EP | 2532312 A2 | 12/2012 |
| WO | 03094743 A1 | 11/2003 |

OTHER PUBLICATIONS

Second Chinese Office Action dated Jul. 4, 2016, issued in Chinese Appln. No. 201380006985.8.
International Search Report dated Jul. 12, 2013, issued in PCT Application No. PCT/US2013/020838.
EP Office Action dated Aug. 16, 2016, issued in EP Application No. 13 701 519.4.
Chinese Office Action dated Jan. 2, 2020, issued in CN Appln. No. 201710063624.
Chinese Office Action dated Jul. 1, 2019, issued in CN Appln. No. 201710063624.
Chinese Office Action Nov. 28, 2018 issued in Chinese Appln. No. 201710063624.

* cited by examiner

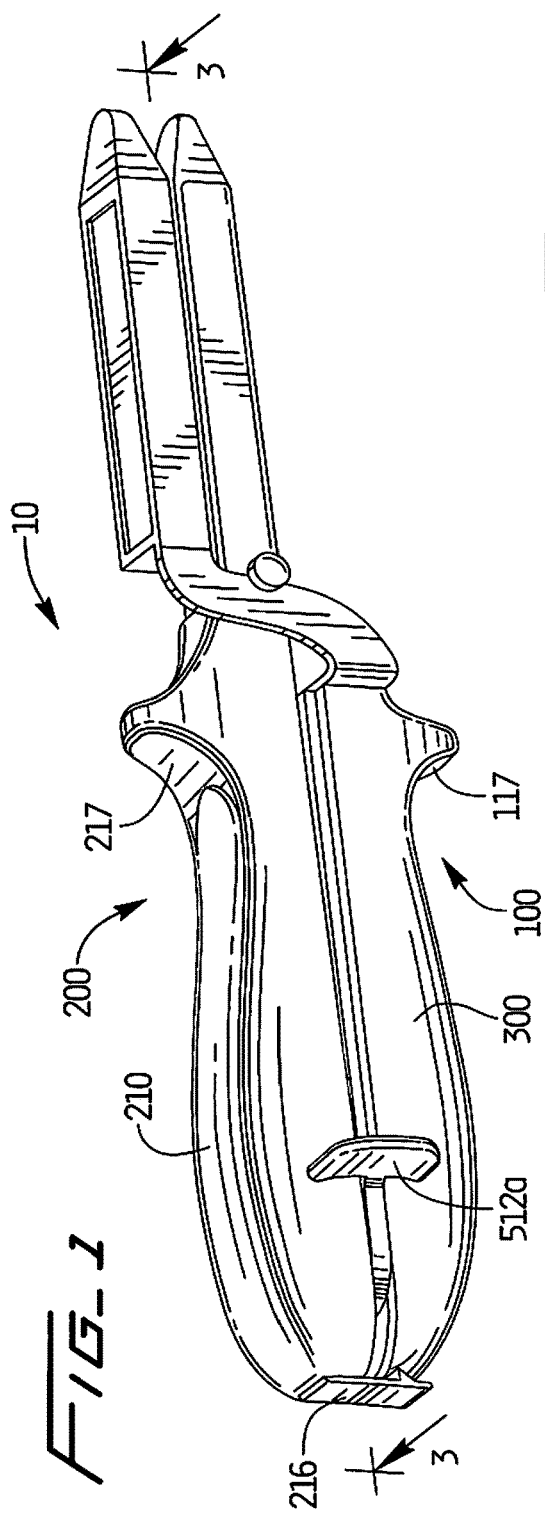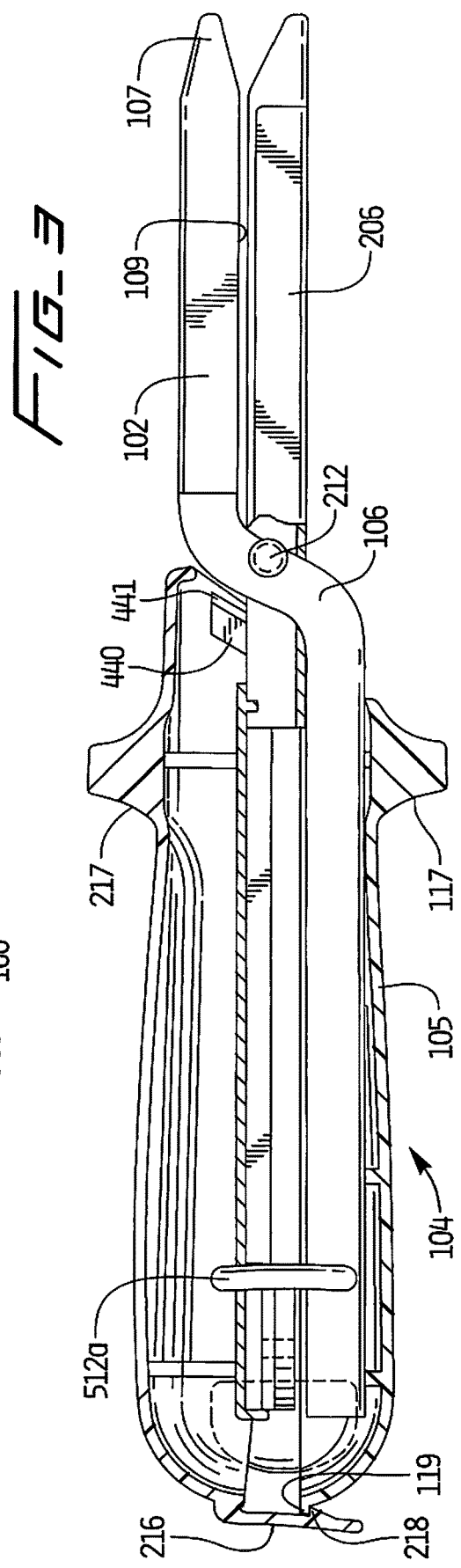

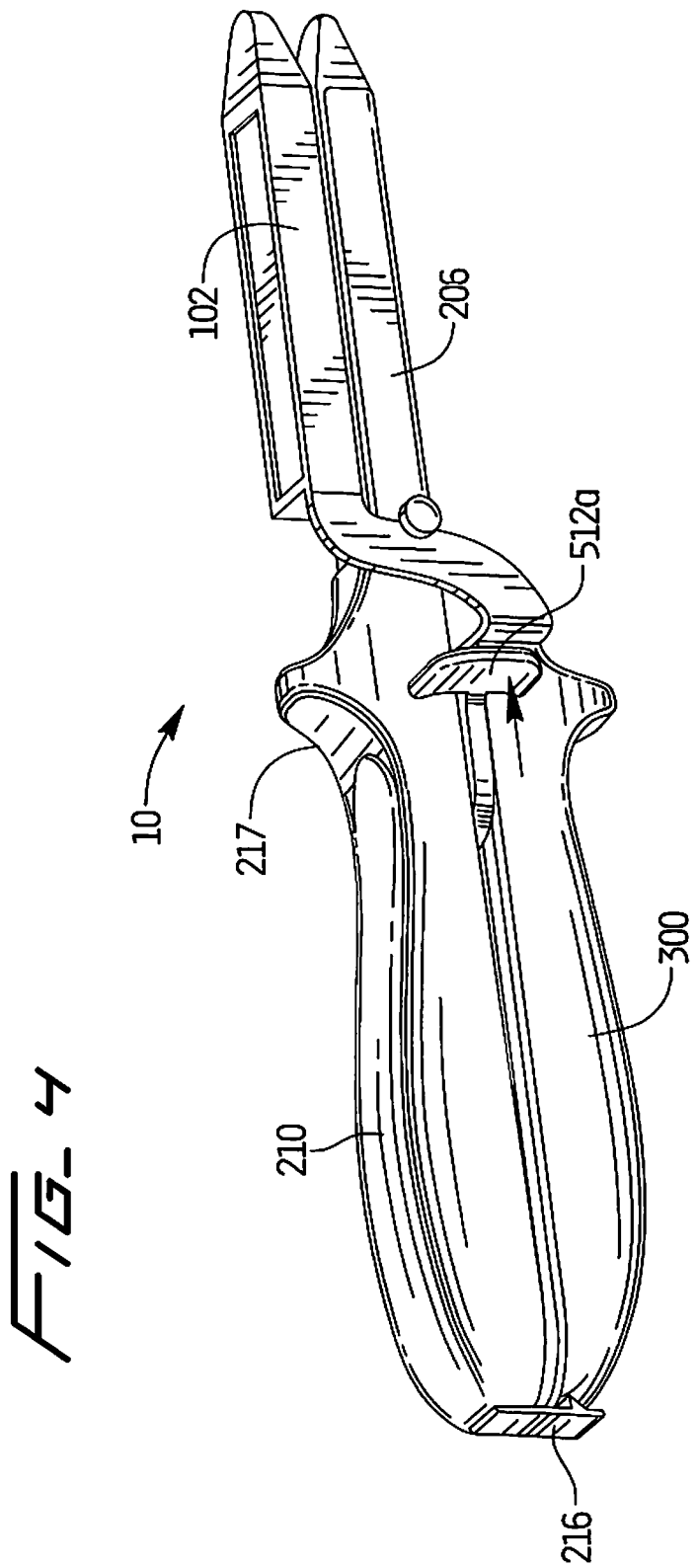

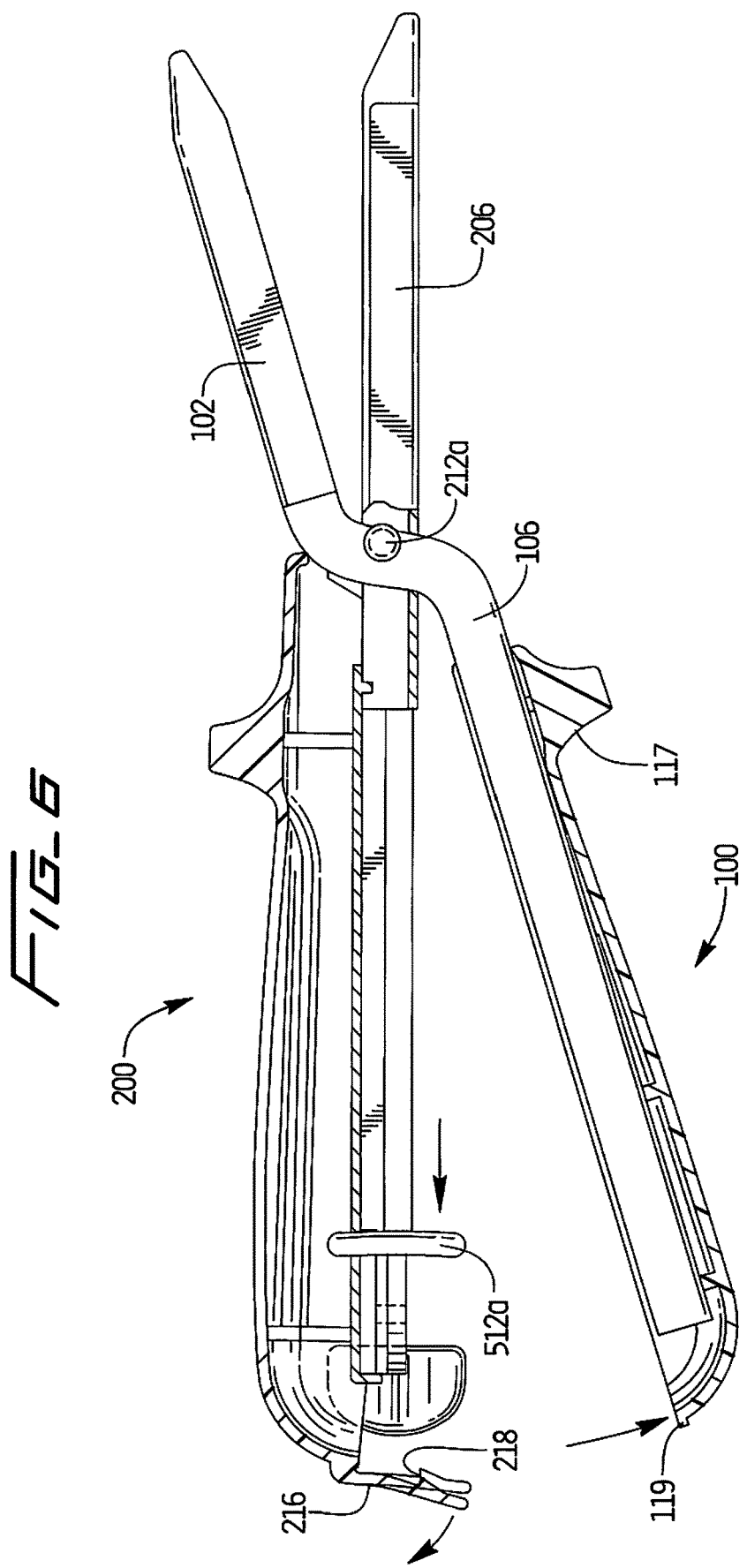

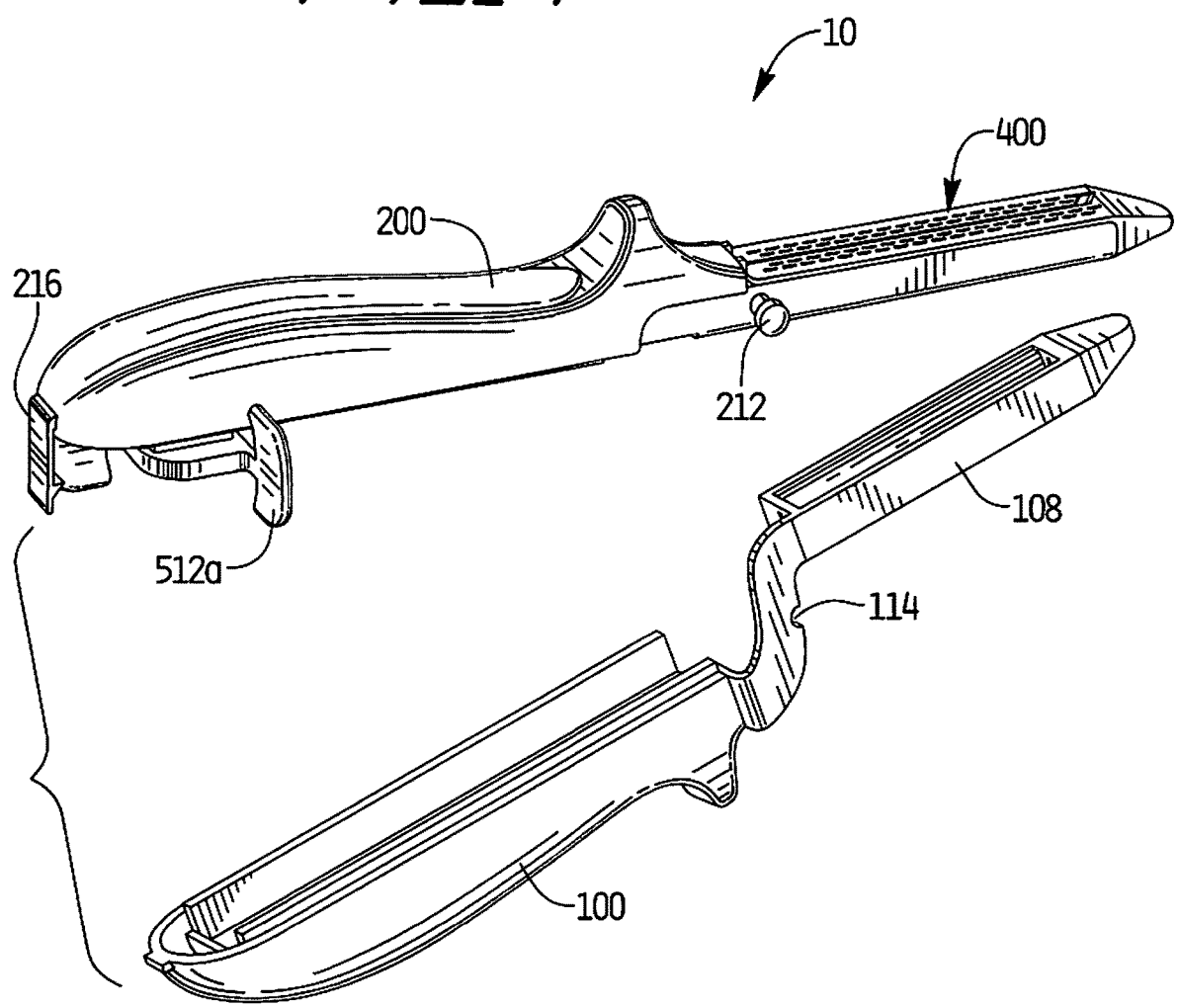

SURGICAL FASTENER APPLYING APPARATUS

CROSS-REFERENCE TO RELATED APPLICATIONS

This application is a continuation of U.S. patent application Ser. No. 14/372,469, filed Sep. 19, 2014, which is a National Stage Application of PCT/US2013/020838 under 35 U.S.C. § 371 (a), filed Jan. 9, 2013, which claims the benefit of and priority to U.S. Provisional Patent Application Ser. No. 61/587,879 filed Jan. 18, 2012. The entire contents of each of the above applications are hereby incorporated by reference.

BACKGROUND

Technical Field

The present disclosure relates to a surgical fastener applying apparatus and, more particularly, to a surgical fastener applying apparatus having both reusable and disposable components.

Background of Related Art

Surgical fastener applying apparatus grasp or clamp tissue between opposing jaw structures and join the tissue by means of surgical fasteners. In some such apparatus, a knife is provided to cut the tissue which has been joined by the fasteners. The fasteners are typically in the form of surgical staples, although other surgical fasteners may also be utilized, such as, for example, clips or two part polymeric surgical fasteners.

Surgical fastener applying apparatus typically include two elongated beam members which are used to capture or clamp tissue therebetween. Typically, one of the beam members carries a disposable cartridge assembly which houses a plurality of staples arranged in at least two lateral rows, while the other beam member includes an anvil which defines a surface for forming the staple legs as the staples are driven from the cartridge assembly. Where two part fasteners are used, the beam member which includes the anvil carries a mating part of the two part fastener, e.g. the receiver. Generally, the staple formation process is affected by the interaction between one or more longitudinally moving camming members and a series of individual staple pushers. As the camming members travel longitudinally through the cartridge carrying beam member, the individual staple pushers are biased upwardly into a backspan of the staples supported within the cartridge assembly to sequentially eject the staples from the cartridge. A knife may be provided to travel with the camming members between the staple rows to cut the tissue between the rows of formed staples. An example of such an instrument is disclosed in U.S. Pat. No. 7,631,794, which is incorporated herein in its entirety by reference.

Although reusable fastener applying apparatus have been developed, such apparatus can be overly complex and prove difficult to sterilize. Because of the difficulties associated with properly sterilizing a fastener applying apparatus for reuse, fastener applying apparatus are typically configured as disposable apparatus. In such disposable apparatus, the cartridge assembly may be replaced to perform multiple fastener applying operations on a single patient, although the fastener applying apparatus is typically disposed after the surgical procedure has been completed. This need for disposability may increase the costs associated with surgical procedures.

Therefore, a need exists in the art for a fastener applying apparatus which includes reusable components, is not overly complex, and is configured to facilitate proper sterilization after use in a surgical procedure.

SUMMARY

In accordance with one aspect of the present disclosure, a surgical fastener applying apparatus is provided comprising a cartridge supporting section and an anvil supporting section, the cartridge supporting section including a distal section and a proximal section and the anvil supporting section and cartridge supporting section configured to clamp tissue therebetween. The anvil supporting section has a distal fastener receiving region, a proximal clamping region and an intermediate region between the fastener receiving region and the clamping region. The proximal clamping region is positioned on a first side of the cartridge supporting section and the fastener receiving region being positioned on a second opposing side of the cartridge supporting section.

In some embodiments, the cartridge receiving section includes a pin extending transversely therefrom and the intermediate region includes a notch for receiving the pin.

In some embodiments, the intermediate region extends alongside the cartridge supporting section. Preferably, the distal section of the cartridge supporting section is configured to receive a disposable loading unit containing a plurality of fasteners and the proximal section is configured to receive a firing unit for firing the plurality of fasteners.

In some embodiments, the firing unit includes a firing knob and a plurality of cam bars movable to fire the fasteners wherein the firing knob and cam bars are disposable.

In some embodiments, the disposable loading unit is loadable into the cartridge supporting section in a first direction and the firing unit is loadable into the cartridge supporting section in a second different direction.

The cartridge supporting section can include a first elongated channel opening to a first side of the cartridge supporting section for supporting a disposable loading unit containing a plurality of fasteners. The cartridge supporting section can include a second channel opening to a second opposite side of the cartridge supporting section for supporting a firing unit.

The anvil supporting section can include an anvil having a plurality of pockets facing the cartridge supporting section.

The surgical fastener applying apparatus can further include a locking mechanism positioned on the proximal end of the anvil supporting and cartridge supporting sections engageable when the sections are moved to the clamped position.

In another aspect, the present disclosure provides a surgical fastener applying apparatus comprising a cartridge supporting section and an anvil supporting section having a distal anvil portion and a proximal handle portion. The cartridge supporting section and anvil supporting section are configured to clamp tissue therebetween when in an approximated position, wherein movement of the proximal handle portion in a first direction toward the cartridge supporting section moves the distal anvil portion in a second opposite direction toward the cartridge supporting section.

In some embodiments, the proximal handle portion forms a clamping lever for pivoting the anvil supporting section relative to the cartridge supporting section wherein the clamping lever is movable from an unclamped position to a clamped position to releasably secure the anvil supporting section in close approximation with the cartridge supporting section.

The apparatus may further include a firing unit including a firing knob and a pair of cam bars operatively connected to the firing knob, the firing knob movable from a first proximal position to a second distal position to fire fasteners supported in the cartridge supporting section. In some embodiments, the firing knob and the cam bars are disposable.

The anvil supporting section can include an anvil having a plurality of pockets, the pockets facing a first side of the cartridge supporting section and the proximal handle portion facing a second opposite side of the cartridge supporting section.

The apparatus may further include a locking mechanism positioned on the proximal end of the anvil supporting and cartridge supporting sections engageable when the sections are moved to the clamped position.

In accordance with another aspect of the present disclosure a top loading surgical fastener applying apparatus is provided comprising a cartridge supporting section including an elongated channel for supporting a disposable loading unit containing a plurality of fasteners. The disposable loading unit is top loaded into the cartridge receiving section on a first top side. An anvil supporting section includes a distal anvil portion and a proximal handle portion movable from an unclamped position to a clamped position to releasably secure the anvil supporting section in close approximation with the cartridge supporting section. The proximal handle portion includes a locking member to engage the cartridge supporting section. A firing assembly includes a firing knob movable from a first proximal position to a second distal position to fire fasteners supported in the disposable loading unit.

In some embodiments, the firing assembly is bottom loaded into the cartridge supporting section.

The apparatus can further include a conical hinge extending transversely from the cartridge supporting section engageable with the anvil supporting section.

Preferably, the firing assembly is disposable and the cartridge supporting and anvil supporting section are sterilizable and reusable.

In some embodiments, the distal anvil portion and a proximal handle portion are integrally formed.

The distal anvil portion can include an anvil having a plurality of pockets facing the cartridge supporting section. An elongated slot can be formed in some embodiments in a surface opposite the anvil pockets and extending longitudinally therealong wherein the anvil slot has a first portion with a transverse dimension greater than a second portion and the second portion is closer to the cartridge supporting section.

BRIEF DESCRIPTION OF THE DRAWINGS

Various embodiments of the presently disclosed surgical fastener applying apparatus are described herein with reference to the drawings wherein:

FIG. 1 is a perspective view of the surgical fastener applying apparatus of the present disclosure shown in the clamped position with the firing knob in the pre-fired position;

FIG. 3 is a longitudinal cross-sectional view of the surgical fastener applying apparatus taken through line 3-3 of FIG. 1;

FIG. 4 is a perspective view similar to FIG. 1 showing the firing knob in the advanced position to fire the fasteners;

FIG. 6 is a view similar to FIG. 3 showing the firing knob retracted and the anvil supporting section unclamped from the cartridge supporting section;

FIG. 7 is a perspective view showing the individual components separated for respective disposal and cleaning.

DETAILED DESCRIPTION

Figure 2:
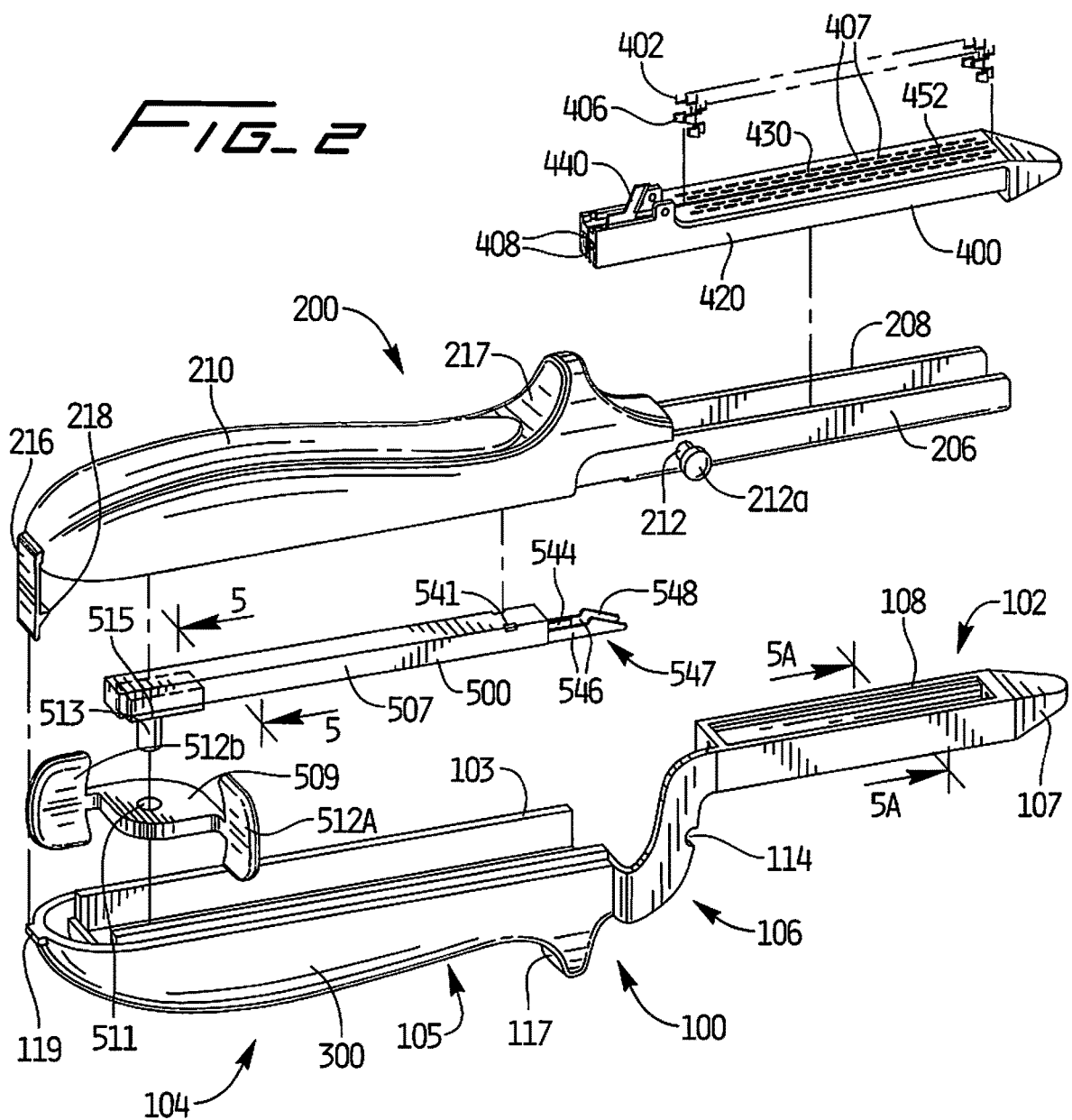
FIG. 2 is an exploded view of the surgical fastener applying apparatus of FIG. 1.

Embodiments of the presently disclosed surgical fastener applying apparatus in accordance with the present disclosure will now be described in detail with reference to FIGS. 1-7, wherein like reference numerals identify similar or identical structural elements. As used herein, as is traditional, the term "proximal" refers to the end of the apparatus which is closer to the user and the term distal refers to the end of the apparatus which is further away from the user.

Turning to FIGS. 1-3, one embodiment of the presently disclosed surgical fastener applying apparatus is shown generally identified as surgical stapler 10. Surgical stapler 10 includes an anvil supporting or half-section 100 and a cartridge supporting or cartridge receiving half-section 200. The anvil supporting section includes a clamping lever 300. That is, as described in more detail below, the anvil supporting section 100 and clamping lever 300 are integral so as to form a single unit. This minimizes the components of the surgical instrument. A disposable assembly includes a single use loading unit 400 (hereinafter "SULU") and a firing unit 500. Each of these components or assemblies will be described in greater detail below.

Anvil half-section 100 and cartridge receiving half-section 200 may be configured as reusable components and, as such, are constructed from biocompatible materials suitable for sterilization and repeated use, e.g., stainless steel. SULU 400 and firing unit 500, on the other hand, are disposable. The SULU 400 and firing unit 500 are separate components. Separation of the anvil half section 100 and cartridge half section 200 of stapler 10 is illustrated in FIG. 7.

SULU 400 and firing unit 500, may be constructed from any suitable biocompatible materials, e.g., plastics, metals, or combinations thereof. Further, surgical stapler 10 may be configured to receive or accommodate disposable assemblies of various different configurations, e.g., disposable assemblies including SULU's and firing assemblies for firing staples of different staple line lengths (e.g., 60 mm, 80 mm and 100 mm).

As will be described in greater detail below, anvil half-section 100 and cartridge-receiving half-section 200 are releasably pivotably engagable with one another in a plier like manner. More specifically, anvil half section 100 includes a distal anvil (fastener receiving) region or portion 102, a proximal clamping region or portion 104 which also forms a handle region, and an intermediate region or portion 106 extending between (joining) the anvil region 102 and the clamping region 104. The anvil half section 100 is pivotably coupled to cartridge-receiving half-section 100 about the intermediate region 106. Clamping region 104 is pivotable relative to cartridge-receiving half-section 200 between a spaced-apart position (FIG. 6) and an approximated position (FIGS. 1 and 3) for moving cartridge-receiving half-section 200 and anvil half-section 100 relative to one another between an open, or un-clamped position and a closed, or clamped position (FIGS. 1 and 3) for clamping tissue therebetween. With surgical stapler 10 in the clamped position, firing unit 500 may be operated to sequentially fire and form a plurality of surgical staples 402 (FIG. 2) about tissue clamped between anvil half-section 100 and cartridge-receiving half-section 200 and for advancing a knife 440 to divide tissue between the stapled portions thereof.

Due to the pliers type arrangement, when the clamping lever 300 of clamping region 104 is moved in a first direction toward the cartridge receiving half section 200 (upwardly in the orientation of FIG. 1), the distal anvil region 102 is moved toward the cartridge receiving section 200 in a second opposite direction (downwardly in the orientation of FIG. 1). This is described in more detail below.

Continuing with reference to FIGS. 1-3, distal anvil region 102 terminates in nose portion 107. Proximal clamping region 104 has an upper surface 103 and an opposing lower surface 105, as viewed in the orientation of FIGS. 1 and 3. Anvil region 102 includes staple deforming portion 108 which includes a plurality of staple deforming recesses 111 defined therein. These recesses 111 are formed on the lower surface, facing toward the tissue clamped between the anvil and cartridge half sections 100, 200. Staple deforming portion 108 is disposed in opposing relation relative to SULU 400 when the SULU 400 is engaged within channel member 206 of cartridge-receiving half-section 200. Further, staple deforming portion 108 includes a central longitudinal slot 130 (FIG. 5) for receiving knife 440 of SULU 400 as the knife 440 is advanced through SULU 400 to divide the stapled tissue. Staple deforming portion 108 can be formed integrally with anvil half-section 100 or, alternatively, may be secured to anvil half-section 100 by any suitable fastening process, e.g., welding.

Figure 5:
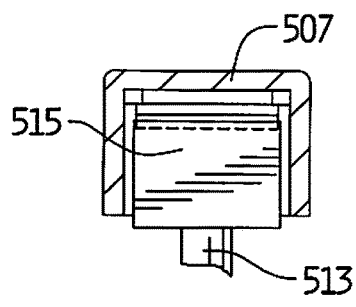
FIG. 5 is a transverse cross-sectional view of the surgical fastener applying apparatus taken along line 5-5 of FIG. 2.
Figure 5A:
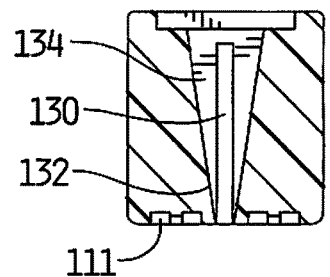
FIG. 5A is a transverse cross-sectional view of the surgical fastener applying apparatus taken along line 5A-5A of FIG. 2.

Staple deforming portion 108 is positioned on the side of anvil half-section 100 facing toward the cartridge receiving half-section 200 (and SULU 400). Knife slot 130, as shown in FIG. 5, extends toward the opposing side of anvil half-section 100. As shown, knife slot 130 has a narrowed region 132 to accommodate sliding movement of the knife 440. Knife slot 130 further progressively increases in width (transverse dimension) away from the cartridge receiving half-section 200 (toward the opposing side of anvil half-section 110) to form a widened slot region 134 to facilitate cleaning of the anvil. Thus, a through slot along the length of the distal anvil region 102 is provided, tapering inwardly to reduce entry of unwanted debris during the procedure, while providing a progressively increased width to facilitate access for cleaning.

A pair of fingers can be disposed adjacent intermediate portion 106 of anvil half-section 100 provide a tissue stop.

Anvil half-section 100 can further include a pair of transversely-spaced extensions which extend towards cartridge receiving section 200. The extensions are configured to contact a surface of a guide block (not shown) as surgical stapler 10 is moved towards the clamped position, such that the guide block is pivoted from a first, locked position to a second, unlocked position. This guide block and its function and structure are described in detail in commonly assigned U.S. Pat. No. 7,055,730 and application Ser. Nos. 61/494,985, filed Jun. 9, 2011 and 61/521,070, filed Aug. 8, 2011, the entire contents of which are incorporated herein by reference.

A central portion of cartridge half-section 200 includes a lateral support member 212, preferably substantially conical in configuration. As shown, the support member 212 with enlarged head 212a extends laterally from a proximal region of the channel member 206. During assembly of anvil half-section 100 and cartridge-receiving half-section 200, lateral support member 212 is supported in notch 114 defined in a intermediate region 106 of anvil-receiving half-section 100 (FIG. 2). Lateral support member 212 provides for pivotal engagement of cartridge receiving half section 200 and anvil receiving section 100 for clamping movement in a plier type manner. The engagement of support member 212 and notch 114 limits lateral movement of the half sections 100, 200. Proximal handle portion 102 of anvil half-section 100 is ergonomically formed and includes a thumb-engaging abutment 117. Cartridge receiving section 200 also has an ergonomically formed thumb engagement member 217.

A proximal end of handle portion 104 includes a locking projection 119. Locking projection 119 extends proximally from the proximal end of clamping portion 300 and is designed to interact with the proximally positioned locking member 216 of cartridge-receiving half section 200 discussed below.

Cartridge-receiving half-section 200 includes an elongated channel member 206 at a distal region (section) having a substantially U-shaped channel 208 defined therein that is configured to releasably receive SULU 400. On the opposing side, at a proximal region (section), a proximal channel is provided to receive the firing unit 500. Consequently, as viewed in the orientation of FIG. 2, the SULU 400 is top loaded into the channel 208 and the firing unit 500 is bottom loaded into the proximal channel.

It is also contemplated, that due to the configuration of the components, the firing unit 500 could alternately be top loaded into a channel formed in the proximal region 104 of the anvil receiving section 102. In this case, the firing knob would be mounted to the anvil section 100 and the cam bars of SULU 400 would extend into the cartridge half section 100 for alignment with the fasteners.

The proximal end of cartridge-receiving half-section 200 includes a locking member 216. Locking member 216 includes shelf 218 configured to engage projection 119 when the anvil half-section 100 is clamped to the cartridge-receiving half-section 200 to provide a ratchet type locking mechanism.

When clamping lever 300 is pivoted from an open position to a clamped position (FIG. 3) projection 119 is forced past locking hook or shelf 218, biasing lock 218 proximally as it passes along the angled wall and past shelf 218. That is, when the stapler 10 is clamped, projection 119 is forced past, then engages (rests atop as viewed in the orientation of FIG. 3) transverse shelf 218 to hold the clamping lever 300 in the locked (clamped) position as the latching of the locking member 216 and projection 119 prevent separation of clamping lever 300 and anvil half-section 100.

To disengage the locking mechanism, the locking member 216 can be pivoted manually by the user away from the projection 119, thereby allowing release of the anvil half section 100.

Referring to FIGS. 2 and 3, firing unit (assembly) 500 includes a knife actuating bar 544, a pair of cam bars 546, and a firing knob 509.

The cam bars 546 extend through slots 408 in SULU 400 to fire fasteners 402 housed in SULU 400. That is, as cam bars 546 are moved distally through SULU 400, they contact pushers 406 contained in SULU 400 to sequentially fire the fasteners 402 through the rows of fastener slots 407 in SULU 400.

A guide block such as guide block 48 of patent application Ser. No. 61/494,985 and guide block 548 of application Ser. No. 61/521,070 can be provided having three longitudinal slots; a slot to receive each of the cam bars 546 and another slot to receive the knife actuating bar 544. The guide block, if provided, can be axially fixed within the distal end of cartridge half section 200 and pivotal from the first position in locking engagement with knife actuating bar 544 to the second position disengaged from knife actuating bar 544 in response to movement of stapler 10 to the clamped position. As anvil supporting 100 is approximated relative to cartridge-receiving half-section 200 to achieve the clamped position, extensions on anvil supporting 100 urge the guide block to pivot from the first engaged position to the second disengaged position to disengage the lockout mechanism to enable firing of the fasteners.

Firing knob 509 includes an aperture 511 to receive post 513. Firing knob 509 is pivotal about post 513 so that the stapler can be fired, i.e. the cam bars 546 advanced distally, from either side of the stapler. That is, finger engagement member 512a or 512b can be selectively engaged by the user to move the firing unit 500 through a firing stroke, depending on the position of firing knob 509. As used herein, a firing stroke is defined as movement of firing knob 552 from a retracted position of FIG. 3 to a fully advanced position of FIG. 4.

Knife actuating bar 544 includes an upturned hook portion and upper and lower notches. A finger projects upwardly from the knife actuating bar 544. When the firing knob 509 is advanced distally, it moves to advance the cam bars 546, and further distal movement effects distal movement of knife actuating bar 544. This arrangement allows for staples to be ejected from SULU 400 prior to cutting of tissue. Details of the knife actuating bar are disclosed in application Ser. No. 61/494,985 previously incorporated herein by reference in its entirety.

Referring to FIG. 2, each cam bar 546 includes a distal portion 547 and a proximal portion supported within housing 507. The proximal end of each cam bar is fixedly attached to slide block 515 from which post 513 extends. Alternately, slide block 515 may be molded about the proximal end of cam bars 546. In one embodiment, the slide block 515 has a pair of slots to receive the cams bars 546. Due to this attachment, when firing knob 509 is advanced distally, it moves cam bars 546 distally through the slots 408 in the SULU 400 so that angled caroming surfaces 548 at the distal portion 547 of cam bars 544 contact pushers 406 to fire the fasteners 402 in a direction substantially perpendicular to the longitudinal axis of the cam bars 546 (substantially perpendicular to the direction of movement of the cam bars 546).

Cartridge-receiving further includes lockout pins 541 formed in housing 507. A slot in the outer surface of each cam bar 546 is engagable with a respective lockout pin 541 to prevent inadvertent advancement of the cam bars 546.

Channel 208 engages and retains SULU 400 therein as wall 206 engages SULU 400 to enclose the underside of cartridge body 420 of SULU 400. Thus, SULU 400 is fixedly secured within channel 206 via a snap-fit engagement. Other securement methods are also contemplated.

SULU 400 includes cartridge body 420, a plurality of staple pushers 406, a knife 440 having an angled sharpened leading edge or blade 441, and a plurality of staples 402. A pivotally mounted safety lockout could also be provided as in safety lockout 128 of the 61/494,985 application and safety lockout 428 of application Ser. No. 61/521,070 (incorporated in their entirety by reference above). Body 420 has a plurality of rows of staple retaining slots 430, e.g., four, six, etc. and a linear slotted knife track 452 centrally disposed therein. Knife 440 includes a downturned hook portion which is positioned to engage upturned hook portion of knife actuating bar 544 of firing unit 500. In the illustrated embodiment, body 420 includes two staggered rows of slots 430 formed on either side of linear slotted knife track 452. The staggered rows of slots 430 extend beyond the distal end of knife track 452 to facilitate staple formation beyond the distal end of the stroke of the knife blade 440a, although other configurations are contemplated.

Staple pushers 406 may be configured to extend into one or more slots 430. In one embodiment, a single pusher is associated with each slot 430. Alternatively, each pusher 406 can be configured to extend into two adjacent slots 430 and is positioned beneath respective staples 402 which are retained in slots 430. Further, each pusher 406 includes a lower cam surface which is positioned for engagement by one of cam surfaces 548 on the distal portion 547 of cam bar 546 such that movement of cam bar 546 through SULU 400 sequentially lifts each respective pusher 406 within its respective slot or slots 430 to eject staples from slots 430.

A proximal end of SULU 400 can include opposed, outwardly extending serrated surfaces to facilitate gripping of the proximal end of SULU 400 to facilitate for removal and/or replacement of SULU 400 (or disposable assembly 600) from channel member 206 of cartridge-receiving half-section 200. The housing 507 of firing unit 500 can also include opposed outwardly extending serrated surfaces to facilitate gripping of firing unit 500 for removal and/or loading into the proximal channel of cartridge receiving half section 200.

A safety lockout 428 of the type described in patent application Ser. Nos. 61/521,070 and in 61/494,985 (lockout 128) can be provided. When the knife 440 is moved towards the advanced position during a firing stroke, the safety lockout can pivot towards the unlocked position. The safety lockout is prevented from pivoting to the unlocked position when the anvil half-section 100 and cartridge-receiving half-section 200 are in the clamped position because the top surface of the safety lockout engages an inner surface of anvil half-section 100 to prevent pivoting of the safety lockout.

The assembly and operation of surgical stapler 10 will now be described. Initially, disposable SULU 400 is engaged within cartridge-receiving half-section 200. In order to engage disposable SULU 400 within cartridge-receiving half-section 200, SULU 400 is generally aligned above cartridge-receiving half-section 200 and is inserted into U-shaped channel 208 of channel member 206. Installation may be facilitated, as discussed above, by grasping serrated surfaces of SULU 400. Firing assembly 500 is separately loaded into cartridge receiving half section 200 by first aligning it below the proximal handle region and inserting it into the proximal channel. Serrated surfaces of housing 507, as discussed above, can facilitate loading. It should be appreciated that reference to top loading and bottom loading are used for the orientation of cartridge receiving section shown in FIG. 2. Clearly, if the orientation changes, such loading references would also change, but the SULU 400 and firing unit 500 will still be loaded in opposing directions on opposite sides of the cartridge receiving section 200.

Once firing unit 500 and SULU 400 are loaded into cartridge half section 200, anvil half-section 100 can be assembled to cartridge-receiving half-section 200. To attach anvil half-section 100 to cartridge-receiving half-section 200, transverse post or support member 212 is positioned in notch 114 of anvil half-section 100. Thereafter, anvil half-section 100 is rotated towards cartridge-receiving half-section 200, thus moving distal anvil region 102 in a second direction toward SULU 400 as the clamping lever 300 is moved in a first direction toward the handle portion 210 of cartridge half section 200. Thus as can be appreciated, the anvil and cartridge half-sections 100, 200 move in a pliers type manner into an approximated position to clamp tissue between anvil region 102 and SULU 400. In this clamped position (e.g. FIG. 3), surgical stapler 10 is ready for use. Note in this position, the firing knob has been rotated to locate either finger engagement member 512a or finger engagement member 512b in position for engagement by the user.

In other words, in use, with surgical stapler 10 in the open, or unclamped position (which corresponds to the position of FIG. 6, although FIG. 6 shows the stapler unclamped after firing), surgical stapler 10 is manipulated into position such that tissue to be stapled and divided is disposed between anvil half-section 100 and cartridge-receiving half-section 200. Thereafter, surgical stapler 10 may be moved to the clamped position to clamp tissue between SULU 400 and staple deforming portion 108 of anvil half section 100. In order to position surgical stapler 10 in the clamped position, clamping lever 300, which is part of anvil half section 100, is rotated in a counter-clockwise direction to the position shown in FIG. 1. As clamping lever 300 is rotated, anvil half section 100 pivots about lateral support member 212. In this position, as shown in FIG. 1, staple deforming portion 108 is positioned in close approximation with the top surface of SULU 400.

As the clamping lever 300 is moved to the clamped position, projection 119 of clamping lever 300 is forced past locking member 216 of cartridge half section 200, flexing the locking member 216 out of the way. After passing by shelf 218, locking member 218 returns to its initial position so that shelf 218 engages and blocks projection 119, thereby preventing separation of the clamping lever 300 and cartridge half-section 200. Thus, in this clamped position, the engagement of shelf 218 and projection 119 locks the clamping lever 300 in the clamped or locked position which locks the anvil half-section 100. This latch is released upon proximal movement of locking member 218 to disengage shelf 218 from projection 119.

If a guide block is provided as discussed above, as surgical stapler 10 is moved to the clamped position, extensions of anvil half-section 100 are approximated relative to cartridge half section 200 such that the extensions eventually contact the upper surface of guide block and urge the guide block to pivot in a generally counter-clockwise direction so it moves from the locked position to the unlocked position, to unlock the knife actuating bar 544. This prevents movement of the knife actuating bar 544 in relation to the guide block prior to clamping, thus ensuring that the knife actuating bar 544 and knife 440 remain properly positioned for operational engagement prior to use.

When stapler 10 is in the clamped, unfired position, firing unit 500 is in the retracted position at the proximal end of the cartridge half-section 200. Firing knob assembly 509 is in a proximal position. Latch portion (hook) 218 of locking member 216 is engaged with projecting surface 119 to retain clamping lever 300 in the clamped position (FIG. 3).

When slide block 515 is in this retracted position, knife 440 and cam surfaces 548 of cam bars 546 are positioned in the proximal end of SULU 400. If a safety lockout is provided, in this position, safety lockout is retained in the locked orientation. In addition, the downturned hook portion of knife 440 is engaged with the upturned hook portion of knife actuating bar 544 to connect firing unit 500 to knife 440 of SULU 400.

When the firing knob 509 is advanced distally to the position of FIG. 4 to fire the fasteners as shown in FIG. 4, slide block 515 is moved distally within a channel of handle portion 210 to move cam bars 546 through slots 408 of SULU 400 and to move to knife actuating bar 544 distally. As cam bars 546 are moved distally, cam surfaces 548 sequentially engage pushers 406 to eject staples 402 from slots 407 of body 420. Concurrently, since the distal end of knife actuating bar 544 is engaged with knife 440, knife 440, after the preset delay, is advanced through SULU 400 to incise tissue between the staple lines.

After firing of the fasteners 402, firing knob 509 is returned to its proximal position of FIG. 1 to retract cam bars 546 and knife 440 after firing. The locking member 216 can be manually released as described above, and the clamping lever 300 rotated counterclockwise away from cartridge half section 200 to separate anvil half-section 100 from cartridge-receiving half-section 200 as clamping lever 300 moves downwardly away from cartridge receiving section 100 and distal anvil region 102 moves upwardly away from SULU 400 as shown in FIG. 6. The anvil half section 100 and cartridge half section 200 can then be separated as shown in FIG. 7 by disengaging lateral member 212 from notch 114. Note in this open position, if the aforementioned safety lockout is provided, the safety lockout moves to its unlocked position such that it projects upwardly from SULU 400 to prevent movement of the stapler 10 back to the clamped position. In order to reuse stapler 10, used SULU 400 must be replaced with a new SULU 400.

During a surgical procedure, SULU 400 and firing unit 500 can be replaced multiple times to facilitate multiple uses of stapler 10 on a single patient. Each disposable SULU 400 is provided with a fresh knife. Further, each fresh firing unit 500 is provided with fresh cam bars 546 and firing knob 509, thus inhibiting fatigue or wear of any of the components thereof and simplifying the number and form of components being resterilized. After the surgical procedure, the SULU 400 and firing unit 500 can be removed from cartridge half section 200 and disposed of in an appropriate manner.

The anvil half-section 100, with integral clamping lever 300, and cartridge receiving half-section 200 on the other hand, can be sterilized, such as by autoclaving, and reused with a new disposable SULU 400 and firing unit 500 in the manner discussed above. Because the firing unit 500 and SULU 400 are all disposable, fewer areas remain on the reusable components for tissue and fluids to become trapped. As such, the reusable components of the apparatus can be more easily sterilized.

It will be understood that various modifications may be made to the embodiments of the surgical fastener applying apparatus disclosed herein. Therefore, the above description should not be construed as limiting, but merely as exemplifications of embodiments. Those skilled in the art will envision other modifications within the scope and spirit of the present disclosure.

What is claimed is:
1. A method of assembling and firing a surgical fastener applying apparatus, the method comprising:

inserting a loading unit having an upper surface defining a plane and a plurality of fasteners into a channel defined by a distal cartridge portion of a cartridge receiving half-section from a first side of the cartridge receiving half-section;

loading a firing assembly into a proximal handle portion of the cartridge receiving half-section from a second side of the cartridge receiving half-section opposite the first side of the cartridge receiving half-section; and assembling the cartridge receiving half-section with an anvil half-section such that a distal anvil region of the anvil half-section is positioned on the first side of the cartridge receiving half-section and a proximal handle region of the anvil half-section is positioned on the second side of the cartridge receiving half-section, wherein the distal anvil region of the anvil half-section is positioned on one side of the plane and the proximal handle region of the anvil half-section is positioned on an opposite side of the plane.

2. The method according to claim 1, wherein inserting the loading unit includes grasping serrated surfaces of the loading unit.

3. The method according to claim 1, further comprising pivoting the distal anvil region of the anvil half-section towards the distal cartridge portion of the cartridge receiving half-section by moving the proximal handle region of the anvil half-section towards the proximal handle portion of the cartridge receiving half-section.

4. The method according to claim 1, wherein assembling the cartridge receiving half-section with the anvil half-section includes engaging an intermediate region of the anvil half-section that is disposed between the distal anvil region and the proximal handle region with a support member of the cartridge receiving half-section.

5. The method according to claim 4, wherein engaging the intermediate region with the support member includes receiving the support member within a notch defined by the intermediate region.

6. The method according to claim 1, further comprising firing the surgical fastener applying apparatus by translating a cam bar of the firing assembly distally to engage the plurality of fasteners.

7. The method according to claim 1, further comprising locking the anvil half-section and the cartridge receiving half-section relative to one another with a locking mechanism positioned on the proximal handle portion of the cartridge receiving half-section and the proximal handle region of the anvil half-section.

8. A method of assembling and firing a surgical fastener applying apparatus, the method comprising:
    loading a firing assembly into an elongated channel of a proximal handle portion of a cartridge section of the surgical fastener applying apparatus;
    moving a proximal handle region of an anvil section of the surgical fastener applying apparatus in a first direction towards the proximal handle region of the cartridge section to move a distal anvil region of the anvil section in a second direction opposite the first direction towards a distal cartridge portion of the cartridge section to clamp tissue between the distal anvil region and the distal cartridge portion; and
    firing the surgical fastener applying apparatus by distally translating a cam bar of the firing assembly through the elongated channel to engage a plurality of fasteners in the distal cartridge portion of the cartridge section.

9. The method according to claim 8, further comprising inserting a loading unit having a plurality of fasteners into a channel defined by a distal portion of the cartridge section from a first side of the cartridge section.

10. The method according to claim 8, wherein firing the surgical fastener applying apparatus includes moving a firing knob of the firing assembly from a proximal position to a distal position to distally translate the cam bar.

11. The method according to claim 8, further comprising disposing of the firing assembly after firing the surgical fastener applying apparatus.

12. The method according to claim 8, further comprising locking the anvil section and the cartridge section relative to one another with a locking mechanism positioned on the proximal handle portion of the cartridge section and the proximal handle region of the anvil section before firing the surgical fastener applying apparatus.

13. A method of assembling and firing a surgical fastener applying apparatus, the method comprising:
    top loading a cartridge having a plurality of fasteners into a channel defined by a distal cartridge portion of a cartridge section of the surgical fastener applying apparatus from a top side of the cartridge section;
    bottom loading a firing assembly into the cartridge section from a bottom side of the cartridge section;
    moving a proximal handle region of an anvil section of the surgical fastener applying apparatus from an unclamped position to a clamped position relative to a proximal handle portion of the cartridge section to approximate a distal anvil region of the anvil section with the cartridge section;
    engaging the cartridge section with a locking member of the proximal handle region of the anvil section; and
    moving a firing knob of the firing assembly from a proximal position to a distal position to fire the plurality of fasteners from the cartridge.

14. The method according to claim 13, wherein bottom loading the firing assembly includes bottom loading the firing assembly into the proximal handle portion of the cartridge section.

15. The method according to claim 13, further comprising assembling the cartridge section with the anvil section by engaging an intermediate region of the anvil section that is disposed between the distal anvil region and the proximal handle region with a support member of the cartridge section.

16. The method according to claim 15, wherein engaging the intermediate region with the support member includes receiving the support member within a notch defined by the intermediate region.

17. The method according to claim 13, further comprising removing the firing assembly after firing the surgical fastener applying apparatus.

18. The method according to claim 13, further comprising sterilizing and reusing the cartridge section and the anvil section after moving the firing knob from the proximal position to the distal position.

* * * * *